United States Patent [19]
Pezzi

[11] 3,930,406
[45] Jan. 6, 1976

[54] CIGARETTE ENDS FIRMNESS DETECTOR

[75] Inventor: Giovanni Pezzi, Bologna, Italy

[73] Assignee: AMF Incorporated, White Plains, N.Y.

[22] Filed: Sept. 5, 1974

[21] Appl. No.: 503,236

[30] Foreign Application Priority Data
Sept. 26, 1974 Italy .................................. 12845/74

[52] U.S. Cl. .................................................. 73/78
[51] Int. Cl.² ......................................... G01N 3/40
[58] Field of Search ..................... 73/78, 81; 209/79

[56] References Cited
UNITED STATES PATENTS 3,116,478  12/1963  Powell ................................ 73/81 X
3,527,347  9/1970   Marradi ............................. 73/81 X
3,703,235  11/1972  McEnery ............................ 209/79

Primary Examiner—Jerry W. Myracle
Attorney, Agent, or Firm—George W. Price; Charles J. Worth

[57] ABSTRACT

A device for detecting the degree of firmness of cigarette ends comprising a rotating drum moving laterally one after the other to a position to be tested, yieldable feeler means with indicator means positioned according to the firmness of a cigarette end being tested and transducer means for providing a signal depending upon the position of the indicator means. The foregoing can be combined with pneumatic means for testing for integrity of the wrappers of cigarettes.

9 Claims, 7 Drawing Figures

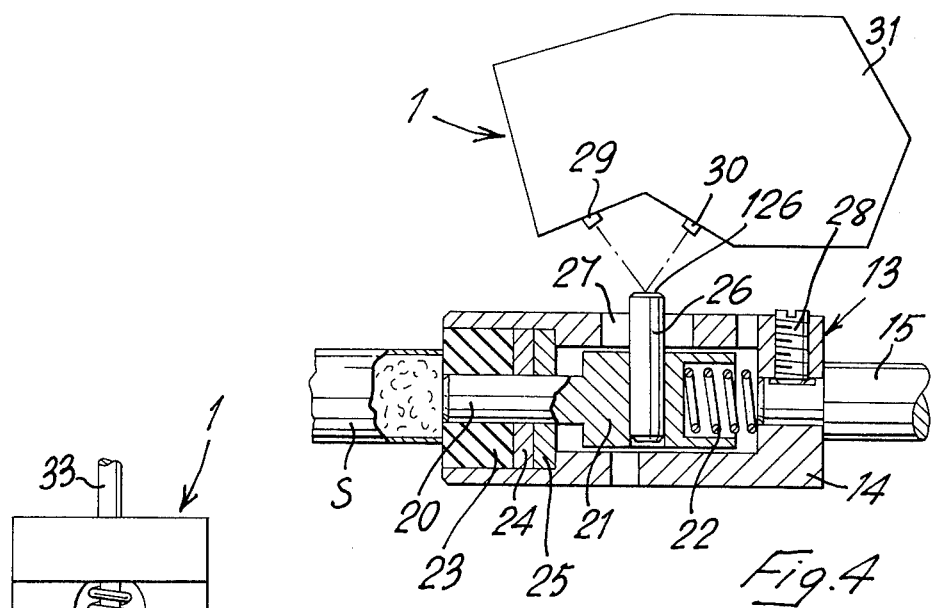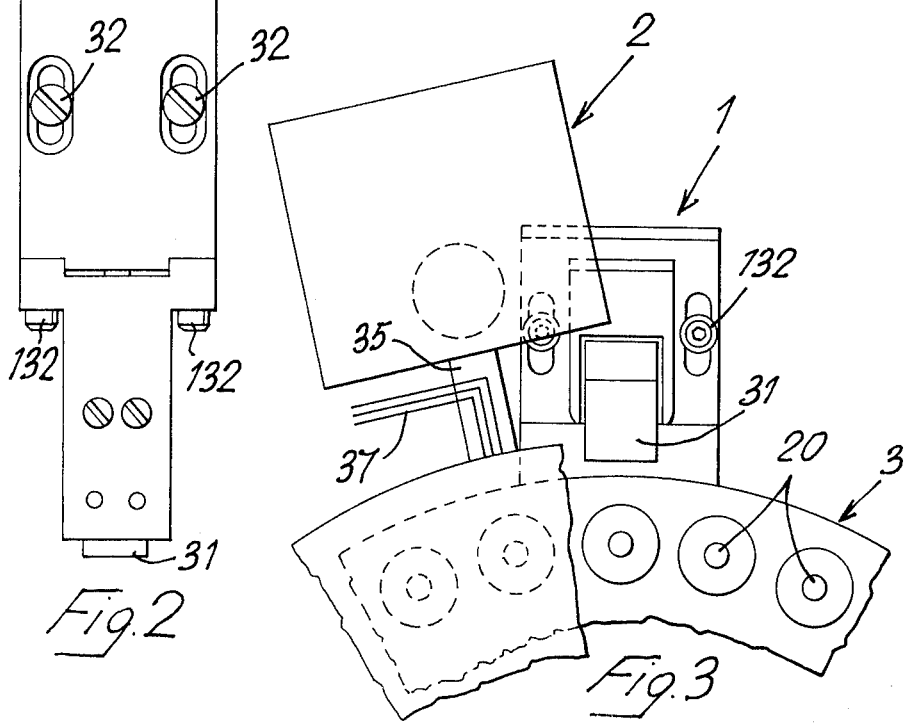

CIGARETTE ENDS FIRMNESS DETECTOR

This invention relates generally to inspection means and more particularly to means for detecting the degree of firmness of cigarette ends.

By the use of the novel end detector, the ends of cigarettes can be detected while on the same drum with which a pneumatic inspection device for the cigarettes is operatively associated. With such operative association, reject signals from the detection and inspection means can be introduced into a common memory with a reject signal from one source lagging a reject signal from the other source depending upon the delay between end detection and penumatic inspection of the cigarettes.

An object of the present invention is to provide improved non-destructive means for detecting the degree of firmness of cigarette ends.

Another object of the present invention is to provide the foregoing means for detecting cigarette ends at the same station the cigarettes are being inspected by a pneumatic inspecting device.

And another object of the present invention is to provide the foregoing detecting means capable of providing reject signals to the same memory and reject means which receives reject signals from the operatively associated pneumatic inspection device.

Substantially, the present invention provides for detection of the cigarette ends to be effected preferably on the same drum or station with which a device for penumatic inspection of the same cigarettes is operatively associated. The novel device for this end detection comprises essentially an elastically yielding feeler, means for bringing the feeler into temporary engagement with the end of a cigarette to be tested during its stay in a sector of the drum, an optically reflecting or refracting element fitted to the end feeler, and optic-beam sensing units operatively associated to the optically reflecting or refracting element to generate signals for acceptance or rejection of the cigarette so engaged by such feeler, in relation to the displacement or not of said feeler, caused by the cigarette end being tested, in one of a plurality of positions for which there exists an acceptable correlation with the degree of firmness of the same cigarette end. Preferably, adjusters are associated to the optic-beam sensing units to extend or restrict the range of a plurality of positions within which the degree of firmness of the cigarette ends is to be considered acceptable. This arrangement is provided with the specific purpose of adjusting said range not only in relation to the degree of firmness of the cigarettes ends, considered from a purely material point of view, but from the point of view of the degree of firmness considered as the best to avoid any tobacco leakage during the long travel of the cigarettes from the packing process to the smoker.

The foregoing and other objects and advantages will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

FIG. 2 is an enlarged plan view of the novel opto-mechanical detector taken on line II—II of FIG. 1.

FIG. 3 is an enlarged fragmentary end view taken on line III—III of FIG. 1.

FIG. 4 is an enlarged longitudinal sectional view of one of the feelers operatively associated with the drum of FIG. 1, and adjustable head means shown in elevation.

Figure 1:
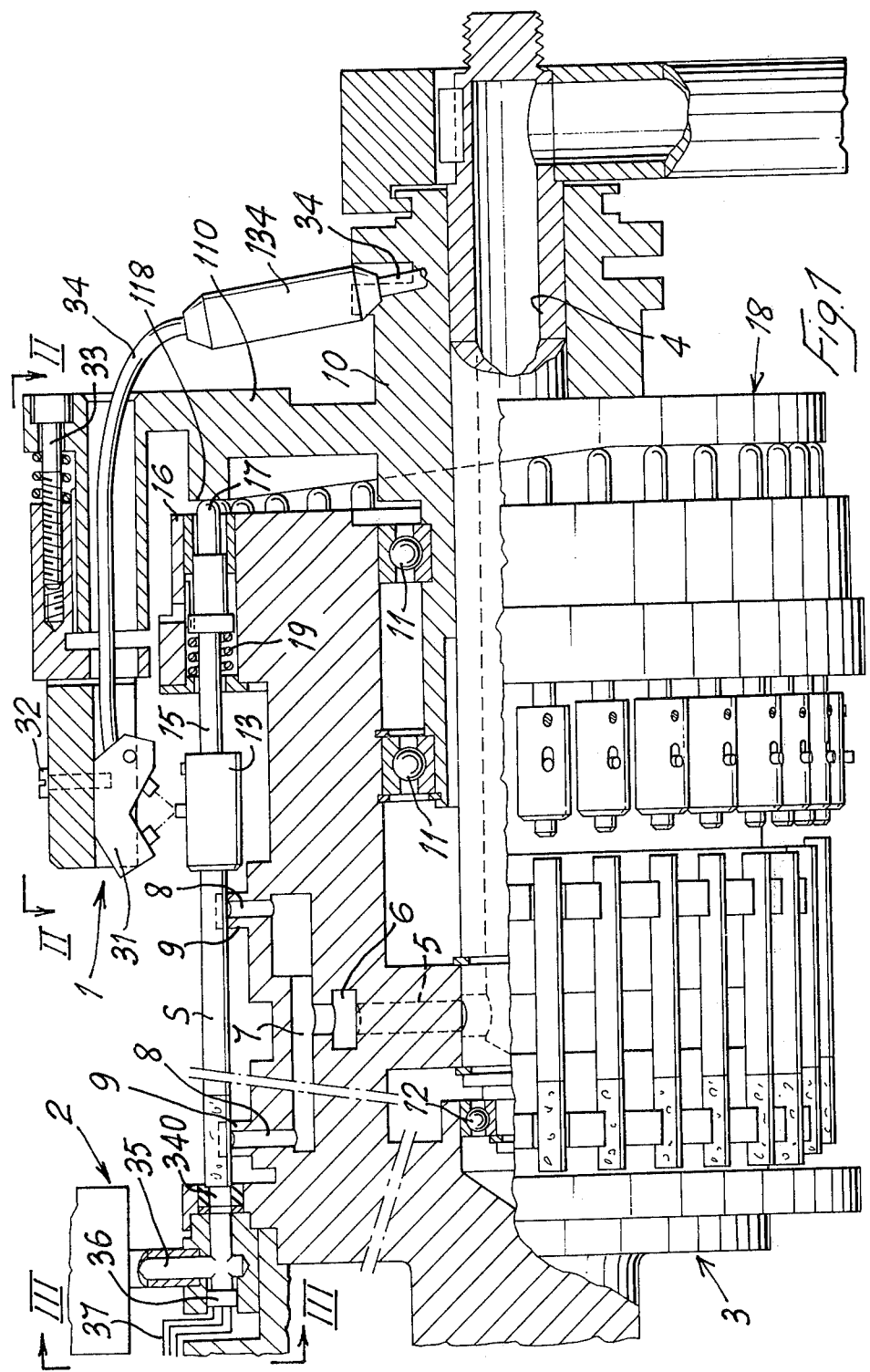
FIG. 1 is an elevational view of a transfer drum with a pneumatic cigarette inspection device and a cigarette end detector, with portions thereof broken away to more clearly illustrate the details thereof.

With reference to the drawings and in particular to FIG. 1, an opto-mechanical cigarette end detector 1 is operatively associated, together with a pneumatic inspection device 2 for single cigarettes, to a pneumatic type fluted drum 3 which is rotatably mounted on a fixed hollow shaft 4. The hollow or bore of shaft 4 is connected with a source of suction (not shown) and transmits suction by means of ducts 5, 6, 7 and 8 to cradles 9 which are provided or disposed in aligned pairs around drum 3. The pairs of cradles 9 receive or accomodate individual cigarettes S to be tested and which are pneumatically held in the cradles by suction provided by ducts 8. Fastened to shaft 4 is a hub 10 provided with bearings 11 and 12 for rotatably supporting the drum 3, and a cam 18 as will be further described.

One end of the drum 3 is provided with an arcuate series of equally spaced pairs of axially aligned cradles 9 while the other end of the drum is enlarged to provide a box or support portion 16 having an arcuate series of spaced axial openings therethrough; each of said openings being axially aligned with a different pair of axially aligned cradles 9.

A plurality of feelers 13 are supported by the drum 3, each in axial alignment with a different pair of axially aligned cradles 9. Each feeler 13 is provided with a cylinder or body 14 having a stem 15 extending therefrom and through one of the axial openings of the box portion 16 of the drum 3. Each stem 15 ends with a tappet or follower portion 17 which is constantly biased against the front face of the cam 18 by spring means such as a coil spring 19, as shown.

The cam 18 is disposed normal to the axis of rotation of the drum 3, its front face or cam surface being circular with two flat arcuate sections of different heights connected together by ramp sections. In other words, the face of cam 18 is provided with two flat circular sections axially spaced from the end of the drum 3. As shown in FIG. 1, the upper flat section 118 is disposed closer to the drum 3 than is the lower flat section.

As the drum 3 rotates, feelers 13 with follower tips 17 moving along the ramp sections between the flat sections are moved axially and engage adjacent ends to be tested for firmness of axially aligned cigarettes S when the follower tips 17 are in contact with the flat section 118 of the face of cam 18.

Figure 5:
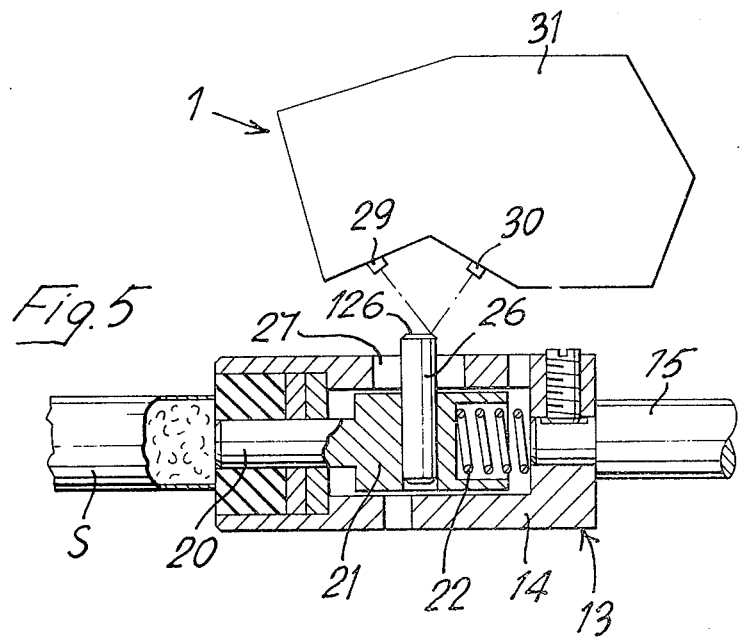
FIGS. 5 and 6 are views similar to FIG. 4 each illustrating the feeler in a different position relative to the head.
Figure 6:
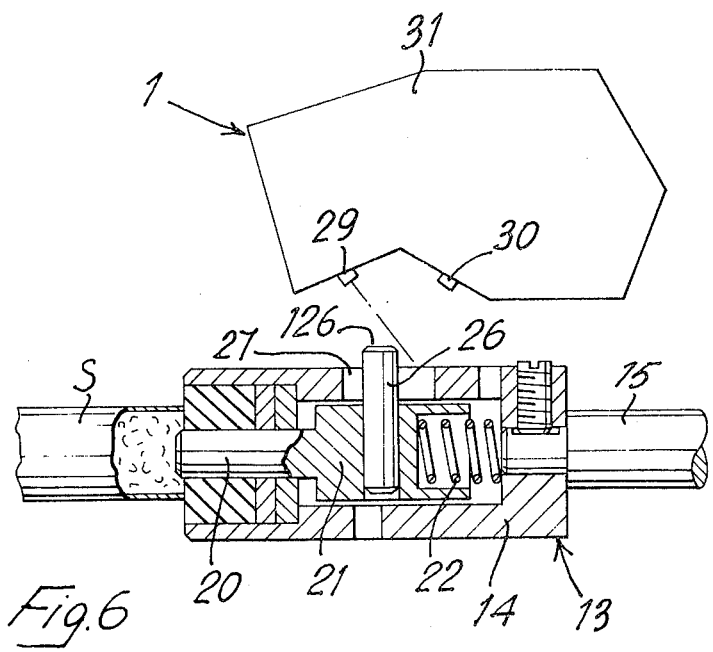
Figure 7:
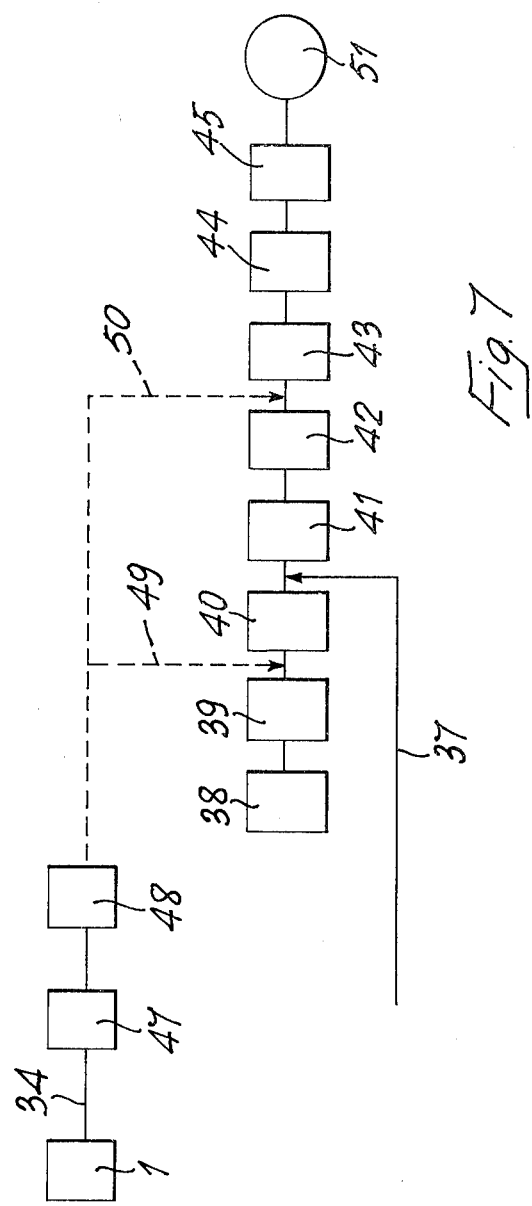
FIG. 7 is a block diagram of a memory and reject means for receiving signals from the inspection and detector devices of FIG. 1.

As best shown in FIGS. 4 to 6, a set screw 28, or other suitable means, connects the end of a cylinder or body 14 to the end of a stem 15 while the other end of the body 14 is provided with a gasket 23, preferably rubber, cemented to a metal disk 24, preferably aluminum, which abuts a washer 25. A plunger 21 movable axially in the housing 14 is normally biased by a spring 22 against the washer 25 and is provided with a feeler pin 20 which extends axially through aligned central openings in the washer 25, disk 24 and gasket 23, and protrudes beyond the end of the housing 14 to engage the adjacent end of a cigarette S axially aligned with the feeler 13. Each housing or body 14 is provided with a longitudinal slot 27, and the plunger 21 therein is provided with a gauge pin 26 which extends laterally through the slot 27 and terminates in preferably a flat face 126 which will be discussed further.

When the end of a cigarette S to be tested is regularly filled with cut tobacco within the desired or predetermined best limits of density and the follower tip 17 of the axially aligned feeler 13 is in contact with the cam face section 118, the feeler pin 20 and plunger 21 will move axially against the bias of spring 22 until the end of the feeler pin is substantially flush with the outer surface of the gasket 23 or the end of the housing 14 to position the pin 26 and its face 126 as shown in FIGS. 4 and 5. When a cigarette S is not properly filled the end of the feeler pin 21 will extend outwardly from the gasket 23 and into the cut tobacco in the cigarette end being tested, as shown in FIG. 6.

The outer end surface 126 of pin 26 is a specular or reflecting surface or, more generally, a surface which influences or has elements which influence the direction and/or the convergency (or other optic features, such as the intensity of absorption) of an optic beam which is deviated or directed by it from a light source 29 to a photosensitive element 30 of the opto-mechanical device 1. In the illustrated embodiment, surface 126 is a flat specular surface through which the incident light from the source 29 is reflected to the photo sensitive element 30 of the opto-mechanical detector device 1. However, (see FIGS. 4, 5 and 6) this light is actually reflected only when the feeler pin 20 is in one of a plurality of preset positions in which the degree of firmness of the cigarette ends are considered to be good or acceptable while there is no reflection when pin 20 is out of the range of said preset positions.

Referring particularly to FIGS. 1 and 2, the light source 29 and photosensitive element 30 are mounted in an adjustable transducer head 31, with slots and screws 32, as well as with a spring adjusting screw coupling 33 on a bracket arm 110 which is integral with hub 10. This adjusting capability allows extension or restriction of the field of action of mirror 126 thus indirectly adjusting, with more or less restrictive concepts, the degree of firmness allowable for the cigarette ends. Slots and screws 132, best shown in FIGS. 2 and 3, are provided to adjust the height or spacing of the head 31 from the feeler means 13.

It should be understood that although the reflection device described has the characteristic qualities of precision of optic systems, the invention is not necessarily restricted thereto but is to be considered in its broadest sense to include any transducer type means suitably sensitive to the position of pin 26 or, more generally, to that of feeler 20. Thus, for instance, suitable magnetic or capacitive units of the types well known in the art, or the like, could be used. The positional adjustment of the beam from the source 29 as shown in FIG. 5 is representative of testing cigarette ends with a very strict or limited acceptable range of the degree of firmness because even a slight amount of yeilding of the cut tobacco under the feeler pin 20 will cause the pin end surface 126 to move out of the beam.

The transducer head 31 or more particularly the beam source 29 and the photosensitive element 30 are connected to an electrical supply circuit and to a memory and rejectiton means, as will be further discussed, by a multipolar cable 34 having a coupling 134, as shown.

With reference to FIGS. 1 and 3, the pneumatic cigarette inspection device 2 associated with the rotary drum 3 substantially inspects filter joints, cork and paper of cigarettes for breaks or apertures. Devices of this kind are known in the art and usually comprise a ported of perforated mouthpiece 340 mounted on drum 3 with one of the openings of the mouthpiece being axially aligned with each pair of aligned cradles 9. During the pneumatic test which, as shown in FIG. 3, takes place at a distinct time in relation to a cigarette end test, pressure air is conveyed to the mouthpiece 340 through a duct 35. Over pressure in duct 35 indicating the wholeness of the cut tobacco wrapper is detected by a transducer 36 which provides a signal which is sent to memory circuits through wires 37.

The original signal supplied by the opto-mechanical transducer 1 is an analog type signal and, consequently cannot be directly introduced into the memory means 38–45 associated with the pneumatic inspection device 2. The memory means preferably is a shift register memory consisting of a plurality of stages which are cascade-connected together in the usual manner. The original signal must, consequently, be converted or adapted to the characteristics of the memory into which it is introduced. For this purpose, said signal is first sent to a shaping circuit consisting of a threshold level circuit 47, such as a Schmidt trigger or the like, which converts the analog signal into a rectangular wave form, of constant amplitude and with sharp edges. The rise and fall edges of this signal can be used to modify the condition of the shift register memory, relating to the cigarette being tested, directly or preferably through a one-shot circuit 48 whose function is to confer a certain duration to the pulse originating from transducer 1, whatever the machine speed may be.

The signal from the one-shot circuit 48 can be introduced into the memory means through either wire 49 or wire 50 which are upstream or downstream, respectively, of the point at which line 37 applies the signal of the pneumatic inspection device 2. The terms "upstream" and "downstream" refer to the shifting direction of the memory means towards the output of the drive signal to a rejection means or solenoid valve 51 which controls compressed air for an ejection nozzle to reject defective cigarettes.

It should be understood, that the present invention is not limited to the embodiment which has been described herein as an example, but can be changed and modified, mainly from a constructive viewpoint, without departing from the spirit of the invention.

For instance, when it is desired to pneumatically inspect the same cigarette whose end is tested for the degree firmness, both tests could be conducted with a single tester which is substantially identical to the opto-mechanical device 1 already described. In this instance the feeler plunger 20 and 21 would be provided with a longitudinal through port. Pressure air would be applied behind the plunger 21 for the pneumatic test and could also be used as a bias for the plunger instead of spring 22. Obviously, the two tests could always be made at distinct times, even though a single device is used. In this case, it would even be convenient to coordinate the two tests such as to conduct the cigarette end test first and then, the penumatic inspection. In fact, if pin 20 penetrates into the end of a cigarette which is defective for lack of firmness, the head 21 could uncover a pressure air exhaust port. By so doing, pressure sensitive transducer 36, conveniently synchronized, could be used to send to the memory a reject signal for lack of firmness, bearing in mind that it will be used, immediately after, in relation to the pneumatic test for cigarette inspection. This test will, obviously, involve only the cigarettes which have passed the firmness test. Naturally, the novel device so modified does not exclude that the end detection from continuing to include the optic means 126, 29 and 30.

Although but a single embodiment of the invention has been illustrated and described in detail, it is to be expressly understood that the invention is not limited thereto. Various changes may also be made in the design and arrangement of the parts without departing from the spirit and scope of the invention as the same will now be understood by those skilled in the art.

I claim:

1. A device for detecting the degree of firmness of cigarette ends, comprising
   a rotating pneumatic drum sequentially moving cigarettes laterally one after another to a position to be tested,
   yieldable feeler means sensitive to the degree of firmness of cigarette ends and having positionable means indicating the degree of firmness of a cigarette being tested,
   circular cam means engaging one end of said feeler means and urging the other end of said feeler means against the end of a cigarette positioned to be tested, and
   transducer means disposed adjacent a cigarette being tested and operatively associated with said feeler means for selectively providing a signal representing the position of said positionable means indicating the degree of firmness of the end of a cigarette being tested,
   said drum being provided with a plurality of axially aligned pairs of cradles disposed in an equally spaced series adjacent one end of the drum,
   said feeler means being a plurality of axially movable feelers supported by said drum each being axially aligned with a different axially aligned pair of cradles, and
   said cam means being provided with a fixed circular cam face having an arcuate portion disposed closer to the adjacent end of said drum than the remainder of said cam face urging a feeler into contact with the end of a cigarette supported by an axially aligned pair of cradles when the cigarette is in a position to be tested.

2. The device in accordance with claim 1, and each of said feelers comprising
   a body defining a chamber therein and having a longitudinal slot through the wall thereof,
   a stem connected at one end to one end of said body and extending axially therefrom into engagement with said cam face at the other end thereof,
   a plunger axially movable in said chamber and having a feeler pin extending axially through the end of said body opposite from said stem to engage the tobacco in the end of a cigarette to be tested,
   spring means within said chamber biasing said plunger and said feeler pin in a direction away from said stem, and
   said indicating means being connected to said plunger and extending laterally therefrom through said slot.

3. The device in accordance with claim 2, wherein said transducer means comprising a light source and a photo sensitive element providing an electric signal in response to light, and
   said indicator means being a pin positioned by said plunger and having an end surface for directing light from said source to said photo sensitive element when in a predetermined position.

4. The device in accordance with claim 3, and said transducer means further comprising
   means for adjusting the transducer means relative to said feelers in directions parallel to and radially toward and away from the axis of rotation of said drum.

5. The device in accordance with claim 4, and
   said photo sensitive element providing electrical analog signals,
   circuit means for receiving analog signals from said photo sensitive element and providing a delayed pulse type signal when the analog signal indicates that the tip of a cigarette being tested is unacceptable, and
   means responsive to pulse type signals from said circuit means for rejecting cigarettes with unacceptable tips after a predetermined time delay from the time such cigarettes are tested.

6. The device in accordance with claim 5, and
   pneumatic inspecting means for testing for integrity of the wrapper of cigarettes supported by said axially aligned pairs of cradles when such cigarettes are in a position arcuately off-set from the position in which the tips of cigarettes are tested by said feelers.

7. The device in accordance with claim 5, and
   said pneumatic inspection means including a transducer providing an analog signal to said circuit means when a cigarette being tested by said inspection means is unacceptable.

8. The device in accordance with claim 7, and
   said pneumatic inspection means introducing pressure air into the end of a cigarette being tested opposite from the end of the cigarette tested by said feeler means.

9. The device in accordance with claim 7, and
   said pneumatic inspection means introducing pressure air through said feeler means, and
   such pressure air providing the spring means for each of said feelers for biasing the plunger thereof in a direction away from said stems.

* * * * *